US00PP29731P2

(12) United States Plant Patent
Ferguson et al.

(10) Patent No.: US PP29,731 P2
(45) Date of Patent: Oct. 9, 2018

(54) STRAWBERRY PLANT VARIETY NAMED 'DRISSTRAWFIFTYSIX'

(50) Latin Name: ***Fragaria* x *ananassa***
Varietal Denomination: DrisStrawFiftySix

(71) Applicant: Driscoll's, Inc., Watsonville, CA (US)

(72) Inventors: Michael D. Ferguson, Moorpark, CA (US); Renae R. Robertson, Santa Maria, CA (US); Philip J. Stewart, Watsonville, CA (US)

(73) Assignee: Driscoll's Inc., Watsonville, CA (US)

( * ) Notice: Subject to any disclaimer, the term of this patent is extended or adjusted under 35 U.S.C. 154(b) by 0 days.

(21) Appl. No.: 15/731,546

(22) Filed: Jun. 26, 2017

(51) Int. Cl.
*A01H 5/08* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson
PP22,247 P2 11/2011 Ferguson (Continued)

OTHER PUBLICATIONS

Unpublished U.S. Appl. No. 14/999,062, filed Mar. 25, 2016, titled "Strawberry Plant Named 'DrisStrawFifty'".

(Continued)

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of strawberry plant named 'DrisStrawFiftySix', particularly characterized by having a high proportion of marketable fruit of the overall yield and flavor, is disclosed.

6 Drawing Sheets

(56) References Cited

U.S. PATENT DOCUMENTS

| | | | |
|---|---|---|---|
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| 2003/0079263 | P1 | 4/2003 | Gilford et al. |
| 2013/0276182 | P1 | 10/2013 | Fear et al. |

OTHER PUBLICATIONS

Unpublished U.S. Appl. No. 15/731,415, filed Jun. 6, 2017, titled "Strawberry Plant Variety Named 'DrisStrawFiftyThree'".

Unpublished U.S. Appl. No. 15/731,421, filed Jun. 6, 2017, titled "Strawberry Plant Variety Named 'DrisStrawFiftySeven'".

Unpublished U.S. Appl. No. 15/731,542, filed Jun. 26, 2017, titled "Strawberry Plant Variety Name 'DrisStrawFiftyTwo'".

Unpublished U.S. Appl. No. 15/731,545, filed Jun. 26, 2017, titled "Strawberry Plant Variety Named 'DrisStrawFiftyOne'".

Unpublished U.S. Appl. No. 15/731,559, filed Jun. 27, 2017, titled "Strawberry Plant Variety Named 'DrisStrawFiftyFour'".

Unpublished U.S. Appl. No. 15/731,560, filed Jun. 27, 2017, titled "Strawberry Plant Variety Named 'DrisStrawFiftyFive'".

STRAWBERRY PLANT VARIETY NAMED 'DRISSTRAWFIFTYSIX'

Latin name:

Botanical classification: *Fragaria* x *ananassa.*

Varietal denomination: The varietal denomination of the claimed variety of strawberry plant is 'DrisStrawFiftySix'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawFiftySix'.

Strawberry plant variety 'DrisStrawFiftySix' was discovered in Ventura County, Calif. in November of 2009 and originated from a cross between the proprietary female parent '516Q53' (unpatented) and the proprietary male parent 'DrisStrawTwentyOne' (U.S. Plant Pat. No. 23,506). A single plant was selected and asexually propagated via stolons in Shasta County, Calif. in 2009.

'DrisStrawFiftySix' was subsequently asexually propagated via stolons, and underwent further testing at a farm in Santa Barbara County, Calif. for six years (2011 to 2016). The present invention has been found to be stable and reproduce true to type through successive asexual propagations via stolons and tissue culture.

'DrisStrawFiftySix' exhibits the following distinguishing characteristics when grown under normal horticultural practices in Santa Barbara County, Calif.:

1. Small, vivid red fruit with an almost cylindrical shape;
2. Flat globose plant habit; and
3. Mid-season harvest maturity.

'DrisStrawFiftySix' was selected for its high proportion of marketable fruit of the overall yield and its flavor.

DESCRIPTION OF THE DRAWINGS

This new strawberry plant is illustrated by the accompanying photographs which show fruit of the plant, as well as the flowers and leaves. The colors shown are as true as can be reasonably obtained by conventional photographic procedures. The photographs are of plants that are 13 weeks old.

DESCRIPTION OF THE NEW VARIETY

Figure 1:
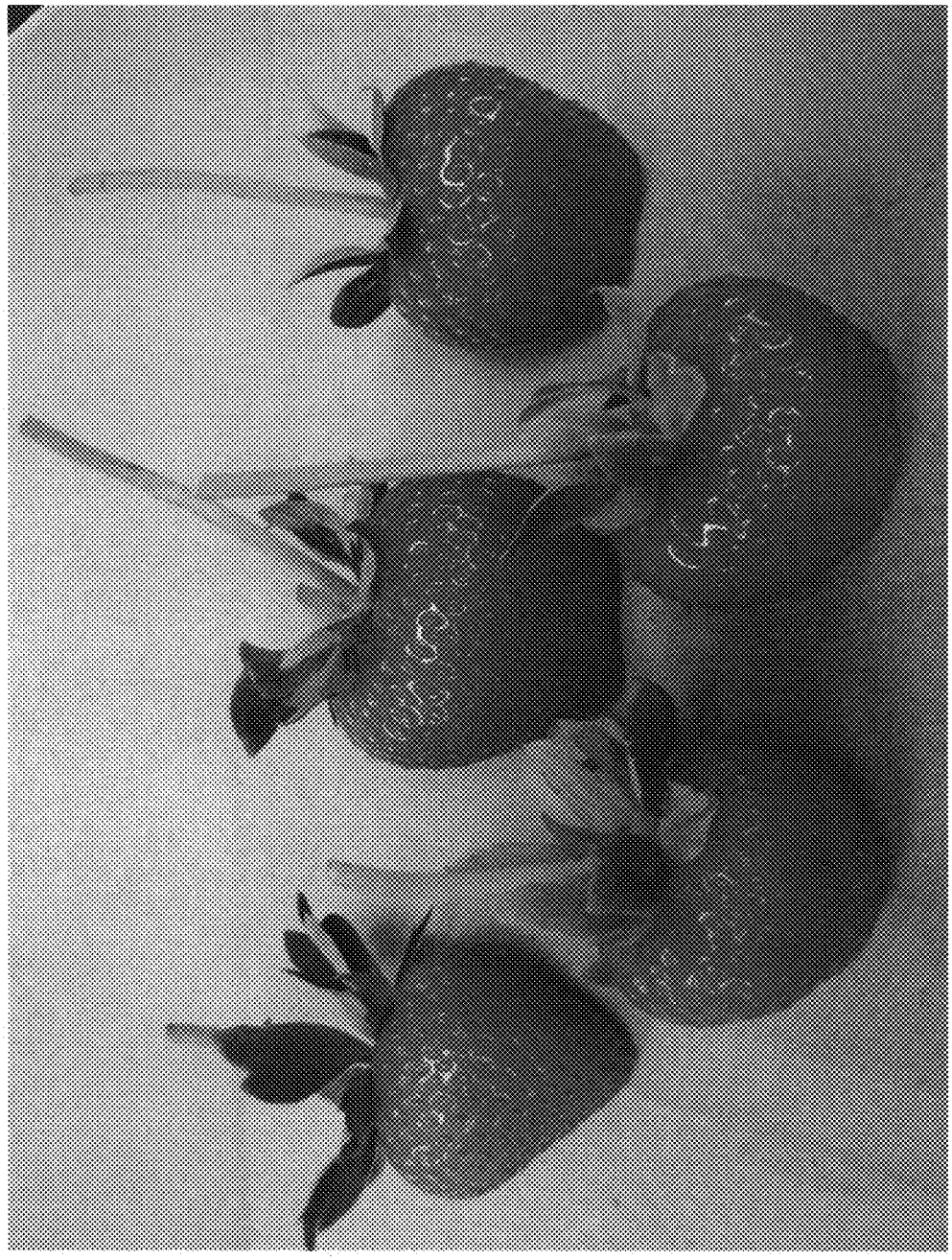
FIG. 1 illustrates whole fruit of variety 'DrisStrawFiftySix'.
Figure 2:
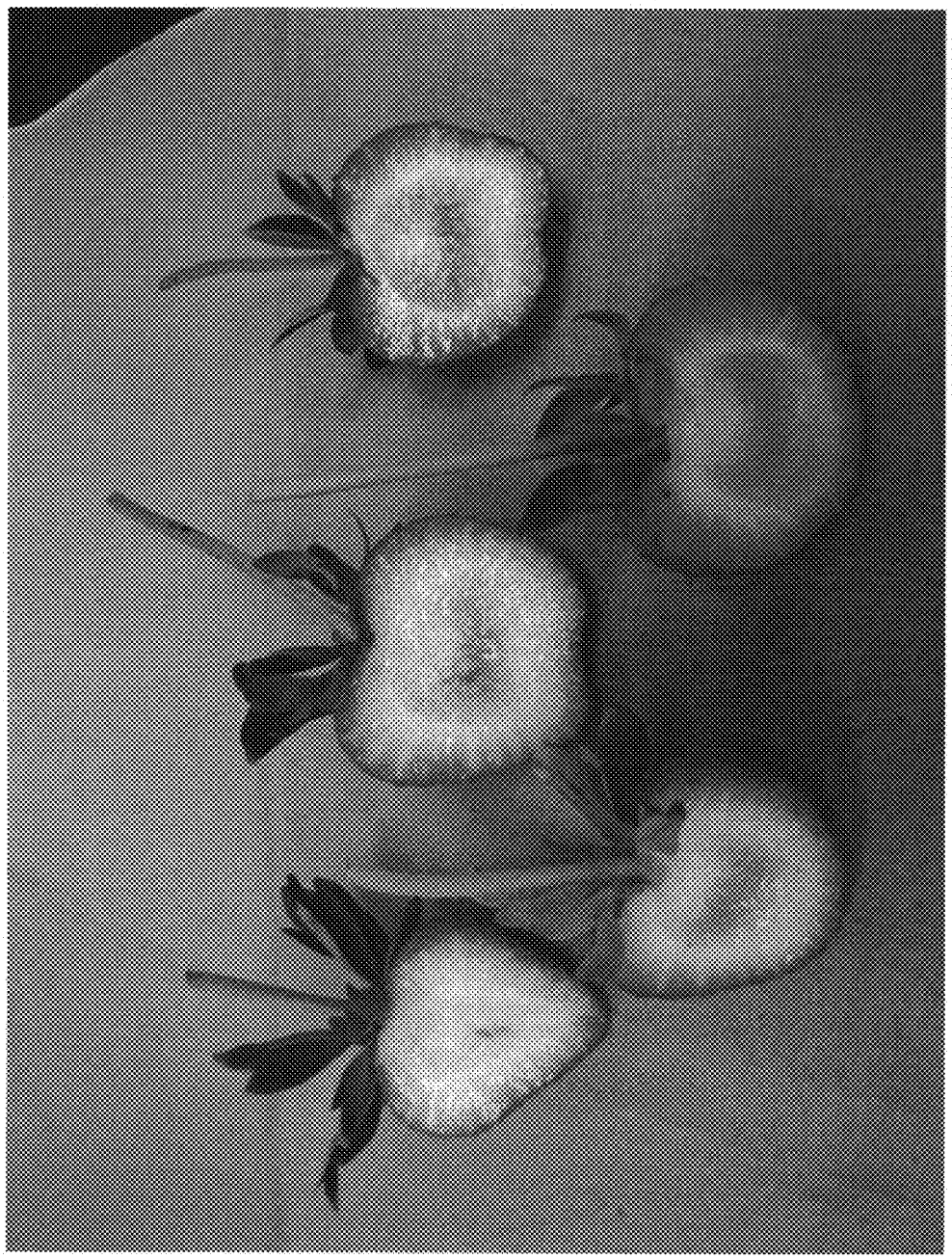
FIG. 2 illustrates longitudinal cross-sections of fruit of variety 'DrisStrawFiftySix'.
Figure 3:
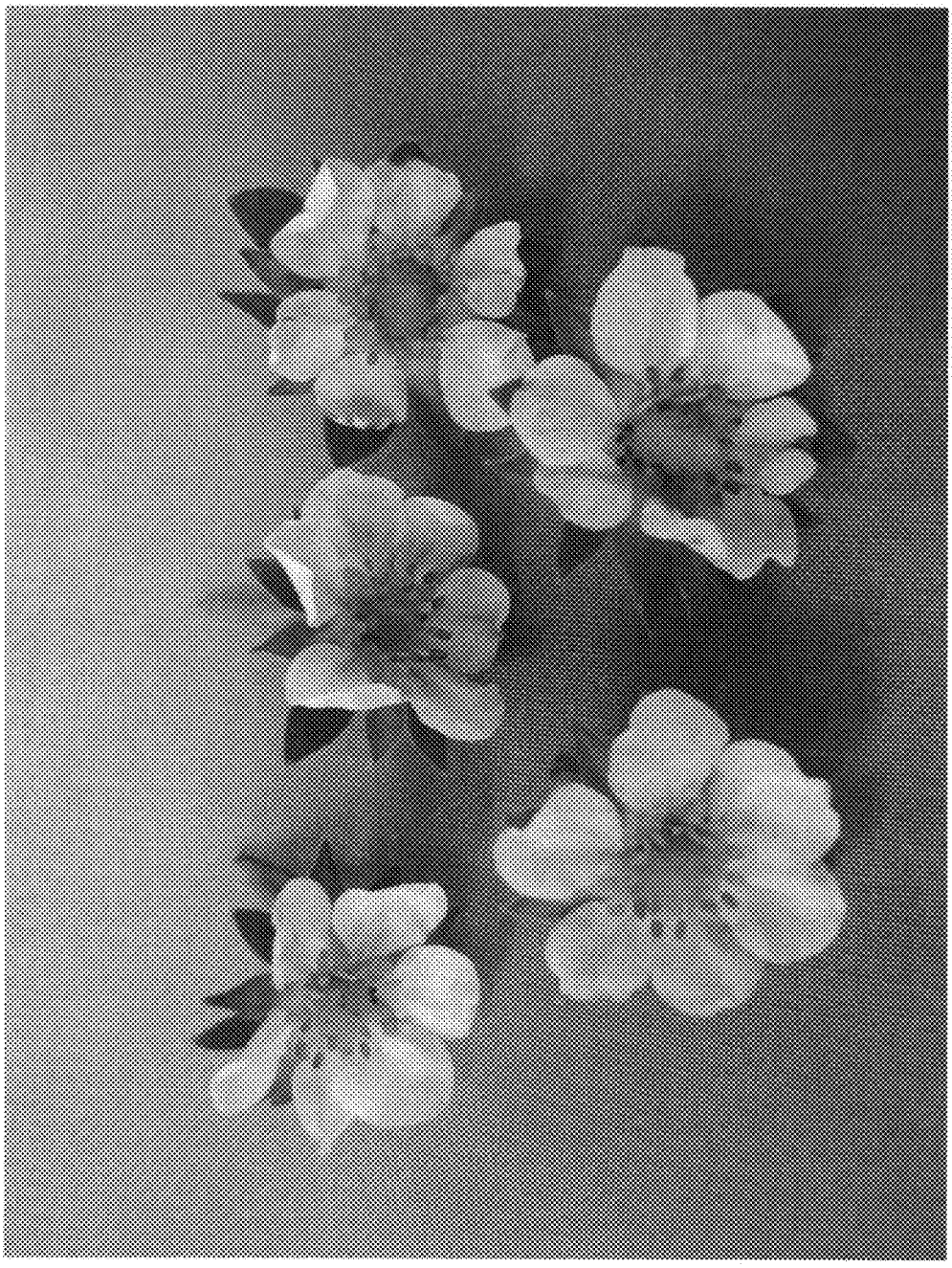
FIG. 3 illustrates upper surfaces of flowers of variety 'DrisStrawFiftySix'.
Figure 4:
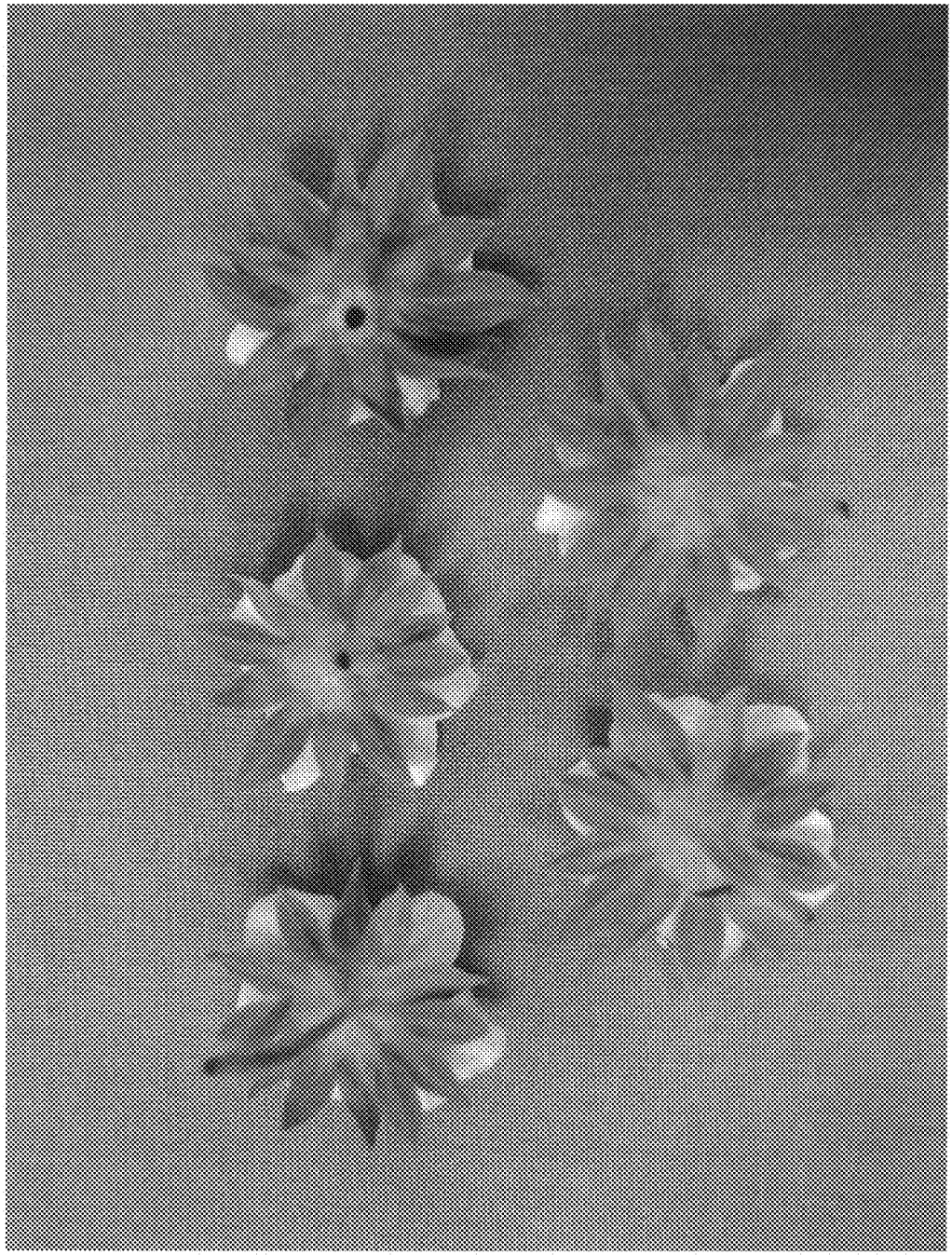
FIG. 4 illustrates lower surfaces of flowers of variety 'DrisStrawFiftySix'.
Figures 5A, 5B:
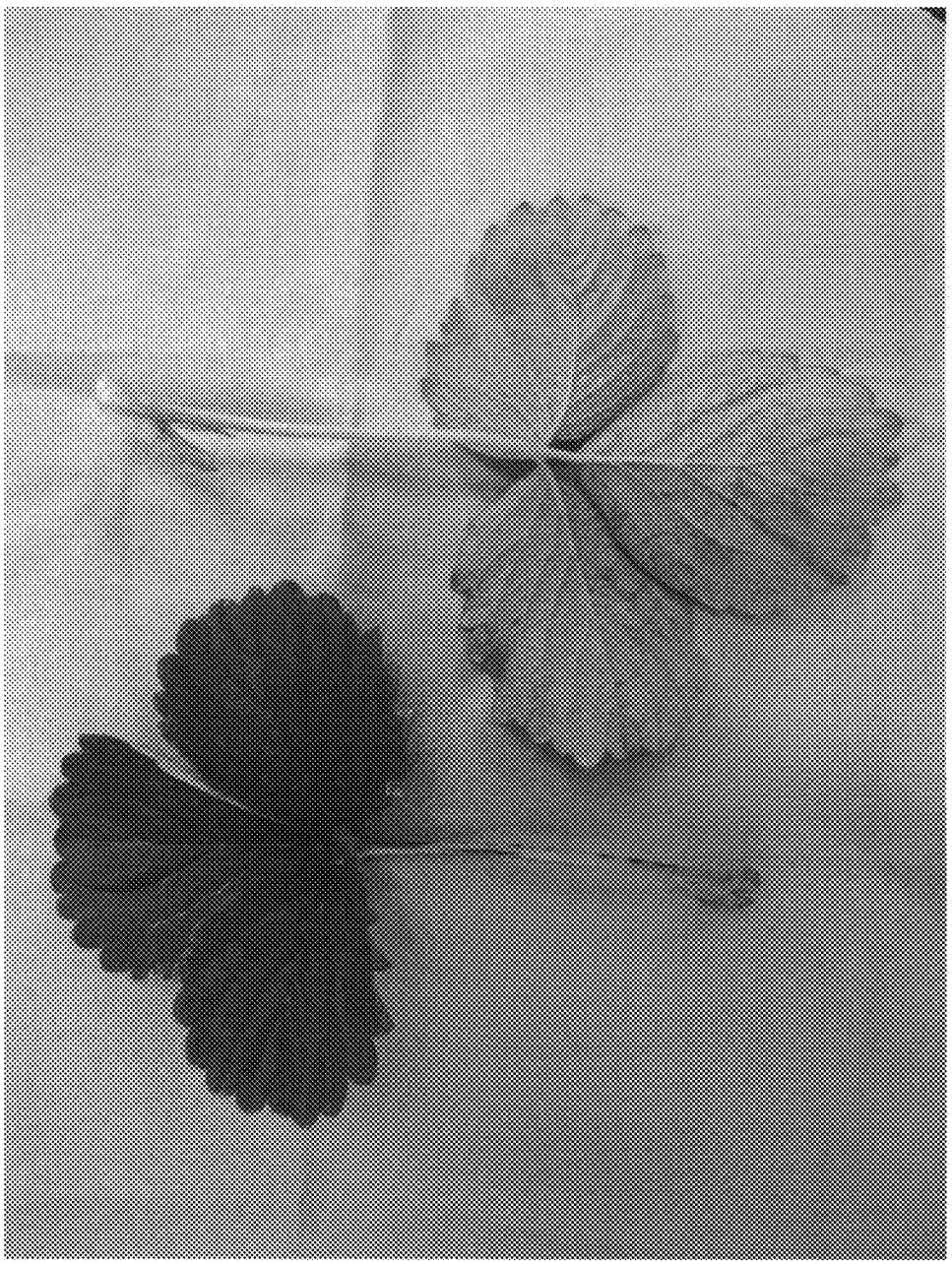
FIG. 5A shows the upper surface of a leaf of variety 'DrisStrawFiftySix' with three leaflets.
FIG. 5B shows the lower surface of a leaf of variety 'DrisStrawFiftySix' with three leaflets.
Figure 6:
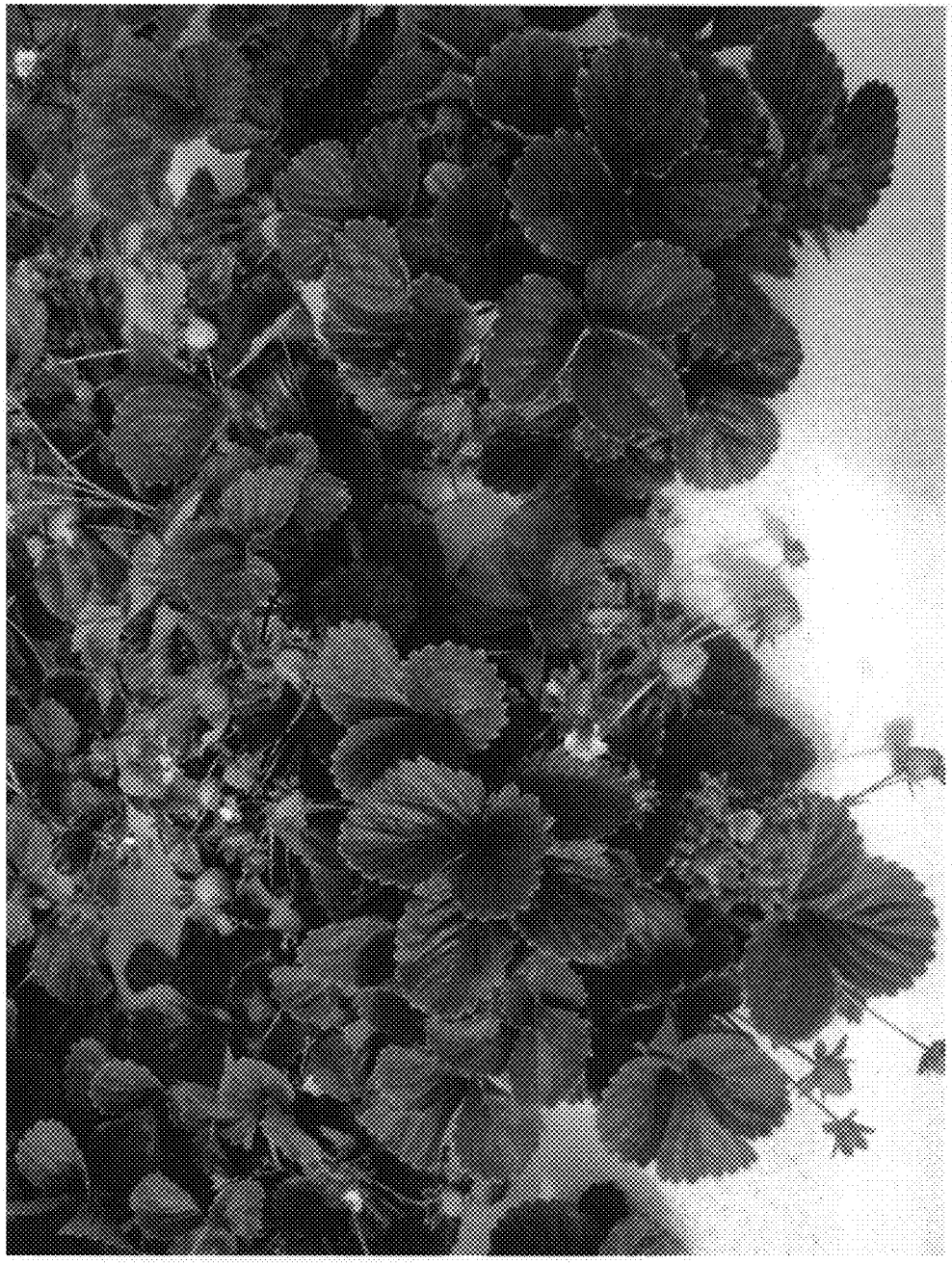
FIG. 6 illustrates the overall plant habit including fruit at various stages of development of variety 'DrisStrawFiftySix'.

The following detailed descriptions set forth the distinctive characteristics of 'DrisStrawFiftySix'. The data which define these characteristics is based on observations taken in Santa Barbara County, Calif. from 2011 to 2016. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFiftySix' has not been observed under all possible environmental conditions. The botanical description of 'DrisStrawFiftySix' was taken from plants that were 13 weeks old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawFiftySix'.

Parentage:

*Female parent.*—The proprietary variety '516Q53' (unpatented).

*Male parent.*—The proprietary variety 'DrisStrawTwentyOne' (U.S. Plant Pat. No. 23,506).

Plant:

*Height.*—21.7 cm.

*Diameter.*—35.4 cm.

*Number of crowns/plant.*—4.

*Habit.*—Flat globose.

Terminal leaflets:
*Length.*—8.5 cm.
*Width.*—8.8 cm.
*Length/width ratio.*—1.0.
*Number of teeth/terminal leaflet.*—18.
*Shape of teeth.*—Obtuse — serrate to crenate.
*Color.*—Upper surface: RHS NN137D (Greyish olive-green). Lower surface: RHS 147B (Moderate yellow-green).
*Shape in cross section.*—Slightly concave.
*Number of leaflets.*—Three only.
*Shape.*—Obicular.
*Base shape.*—Rounded.
*Apex descriptor.*—Rounded.
*Margin.*—Serrate.
*Margin profile.*—Cupped.
*Variegation.*—Present.

Petiole:
*Length.*—12.4 cm.
*Diameter.*—8.52 mm.
*Pose of hairs.*—Slightly upwards.
*Color.*—RHS 144B (Strong yellow-green).
*Bract frequency* (*number present on each petiole*).—0.

Petiolule:
*Length.*—12.99 mm.
*Diameter.*—7.24 mm.
*Color.*—RHS 144B (Strong yellow-green).

Stipule:
*Length.*—3.4 cm.
*Width.*—14.42 mm.
*Stipule anthocyanin coloration.*—Present.

Stolon:
*Average number of daughter plants per square foot.*—10.
*Anthocyanin coloration.*—Present. Color: RHS 173A (Dark reddish orange).
*Diameter at bract.*—0.15 mm.

Inflorescence:
*Position relative to foliage.*—Level with.
*Flower diameter.*—26.60 mm.
*Number of flowers per plant.*—2.60.
*Petals.*—Shape: Obicular. Apex: Rounded. Base: Concavo-convex. Margin: Entire. Spacing: Touching. Length: 8.95 mm. Width: 10.14 mm. Length/width ratio: 0.9. Petal number per flower: 5. Color (upper surface): RHS 157D (Greenish white).
*Calyx.*—Diameter: 29.33 mm. Insertion of calyx: In a basin — inserted. Pose of calyx segments: Reflexed — upwards.
*Sepal.*—Shape: Elliptical. Apex: Convex. Margin: Entire. Length: 10.66 mm. Width: 5.65 mm. Sepal number: 12.
*Receptacle color.*—RHS 1A (Brilliant greenish yellow).
*Stamen.*—Present. Anther color: RHS 13A (Vivid yellow).
*Pedicel.*—Attitude of hairs: Upwards.
*Time of flowering* (*50% of plants at first flower*).—Early.
*Flowering interval.*—February to September.

Fruiting truss:
*Length.*—25.8 cm.
*Diameter at base of truss.*—5.06 mm.
*Number of berries per fruiting truss.*—6.
*Attitude at first picking.*—Erect.
*Color at base of truss.*—RHS 151A (Strong greenish yellow).

Fruit:
*Length.*—37.82 mm.
*Width.*—39.31 mm.
*Length/width ratio.*—1.0.
*Fruit hollow length.*—5.21 mm.
*Fruit hollow width.*—3.53 mm.
*Fruit hollow length/width ratio.*—1.5.
*Fruit weight.*—27.6 g.
*Predominant fruit shape.*—Almost cylindrical.
*Fruit skin color.*—RHS 45B (Vivid red).
*Achenes.*—Insertion of achenes: Below surface. Coloration (sunward side of berry): RHS 58A (Moderate purplish red). Coloration (shaded side of berry): RHS 154C (Brilliant yellow-green).
*Color of flesh* (*excluding core*).—RHS N155D (Yellowish white).
*Color of core.*—RHS 41C (Moderate reddish orange).
*Number of achenes per berry.*—283.
*Distribution of flesh color.*—Marginal and central.
*Type of bearing.*—Fully everbearing — fully remontant.
*Harvest maturity* (*beginning of fruit ripening when 50% of plants have ripe fruit*).—Mid-season.
*Harvest interval.*—March to September.
*Production.*—643.852 grams/plant.

COMPARISON WITH PARENTAL AND COMMERCIAL VARIETIES

When 'DrisStrawFiftySix' is compared to the female parent '516Q53' (unpatented), 'DrisStrawFiftySix' produces a higher yield of fruit with a shorter shelf-life, and that is sweeter than '516Q53'.

When 'DrisStrawFiftySix' is compared to the male parent 'DrisStrawTwentyOne' (U.S. Plant Pat. No. 23,506), 'DrisStrawFiftySix' produces a lower yield of fruit with a higher proportion of marketable fruit and that is sweeter than 'DrisStrawTwentyOne'. Additionally, 'DrisStrawFiftySix' reaches harvest maturity at mid-season, while 'DrisStrawTwentyOne' reaches harvest maturity late in the season.

When 'DrisStrawFiftySix' is compared to the commercial variety 'DrisStrawThirtyOne' (U.S. Plant Pat. No. 24,317), 'DrisStrawFiftySix' produces fruit that is smaller and has a lighter red color than 'DrisStrawThirtyOne'. Additionally, 'DrisStrawFiftySix' produces plants with a flat globose plant habit and produces fruit with an almost cylindrical shape, while 'DrisStrawThirtyOne' produces plants with an upright plant habit and produces fruit with a conical shape.

We claim:

1. A new and distinct variety of strawberry plant named 'DrisStrawFiftySix' as shown and described herein.

* * * * *